United States Patent [19]

Huellmann et al.

[11] Patent Number: 5,455,352

[45] Date of Patent: Oct. 3, 1995

[54] PREPARATION OF N-(2-HYDROXYETHYL)-PIPERAZINE

[75] Inventors: Michael Huellmann, Heppenheim; Rainer Becker, Bad Duerkheim; Emil Scharf, Ludwigshafen, all of Germany

[73] Assignee: BASF Aktiengesellschaft, Ludwigshafen, Germany

[21] Appl. No.: 282,073

[22] Filed: Jul. 28, 1994

[30] Foreign Application Priority Data

Jul. 31, 1993 [DE] Germany .................... 43 25 848.4

[51] Int. Cl.⁶ .................................. C07D 295/08
[52] U.S. Cl. ........................................ 544/401
[58] Field of Search ................................ 544/401

[56] References Cited

U.S. PATENT DOCUMENTS

| | | | |
|---|---|---|---|
| 2,541,260 | 2/1951 | Malkemus et al. | 260/268 |
| 3,172,891 | 3/1965 | Brader, Jr. et al. | 260/280 |
| 3,297,701 | 1/1967 | Brader et al. | 544/401 |
| 3,342,820 | 9/1967 | Brader et al. | 544/401 |
| 3,386,800 | 6/1968 | Brader et al. | 544/401 |
| 4,328,370 | 5/1982 | Fazio | 564/486 |
| 4,338,443 | 7/1982 | Brennan et al. | 544/410 |
| 4,709,034 | 11/1987 | Marsella | 544/401 |
| 4,725,681 | 2/1988 | Shubkin et al. | 544/352 |
| 4,945,161 | 7/1990 | Messina et al. | 544/401 |
| 5,068,330 | 11/1991 | Burgess et al. | 544/401 |
| 5,196,588 | 3/1993 | Burgess et al. | 544/401 |
| 5,214,215 | 5/1993 | King et al. | 544/402 |

FOREIGN PATENT DOCUMENTS

| | | |
|---|---|---|
| 1381243 | 3/1963 | France . |
| 249017 | 8/1987 | Germany . |

*Primary Examiner*—Cecilia Tsang
*Attorney, Agent, or Firm*—John H. Shurtleff

[57] ABSTRACT

Preparation of N-(2-hydroxyethyl)-piperazine by reacting triethanolamine with ammonia in the presence of hydrogen at from 100° to 500° C. and from 10 to 500 bar over a heterogeneous catalyst in which the catalytically active material contains from 20 to 85% by weight of $ZrO_2$ or $Al_2O_3$ or mixtures thereof, from 1 to 30% by weight of at least one copper oxide, calculated as CuO, and from 1 to 60% by weight of at least one oxide of cobalt, nickel or molybdenum, calculated as CoO, NiO and $MoO_3$, respectively.

14 Claims, No Drawings

PREPARATION OF N-(2-HYDROXYETHYL)-PIPERAZINE

The present invention relates to a process for the preparation of N-(2-hydroxyethyl)-piperazine by hydrogenation of triethanolamine under aminating conditions in the fluid or gas phase at super-atmospheric pressure and elevated temperatures in the presence of a catalyst which contains $ZrO_2$ and/or $Al_2O_3$, CuO, CoO, NiO and/or $MoO_3$.

FR-A-13 81 243 discloses the reaction of triethanolamine with ammonia in the presence of hydrogen to give a mixture of piperazine (unsubstituted) and 1,4-diazabicyclo[2.2.2]octane (DABCO).

U.S. Pat. No. 4,328,370 discloses the amination of triethanolamine in a hydrogen atmosphere over palladium catalysts to give mixtures of mono- and diethanol compounds.

According to DD-A-249 017, N,N'-bis-(2-hydroxyethyl)-piperazine is obtained in a batchwise reaction, under pressure, from triethanolamine and ammonia over crosslinked polyamides as catalysts.

U.S. Pat. No. 4,725,681 discloses the reaction of a mixture of diethanolamine and triethanolamine to give N-(2-hydroxyethyl)-piperazine, large amounts of DABCO simultaneously being formed.

U.S. Pat. No. 2,541,260 furthermore discloses that piperazine can be reacted with ethylene oxide to give a mixture of N-(2-hydroxyethyl)-piperazine and N,N'-bis-(2-hydroxyethyl)-piperazine.

Moreover, U.S. Pat. No. 4,338,443 discloses the synthesis of N-(2-hydroxyethyl)-piperazine from diethanolamine and ethanolamine over nickel/copper/chromium catalysts, the selectivity achieved being completely unsatisfactory.

The known processes are unsatisfactory owing to the low selectivity in the preparation of N-(2-hydroxyethyl)-piperazine.

It is an object of the present invention to remedy the above-mentioned disadvantages.

We have found that this object is achieved by a novel and improved process for the preparation of N-(2-hydroxyethyl)-piperazine of the formula I

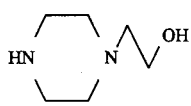

by reacting triethanolamine of the formula II

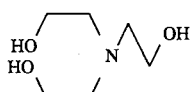

with ammonia in the presence of hydrogen at from 100° to 500° C. and from 10 to 500 bar over a heterogeneous catalyst, wherein a heterogeneous catalyst having an active material containing from 20 to 85% by weight of $ZrO_2$ and/or $Al_2O_3$, from 1 to 30% by weight of oxygen-containing compounds of copper, calculated as CuO, and from 1 to 60% by weight of oxygen-containing compounds of cobalt, calculated as CoO, and/or oxygen-containing compounds of nickel, calculated as NiO, and/or oxygen-containing compounds of molybdenum, calculated as $MoO_3$, is used.

The novel process can be carried out as follows: triethanolamine II and ammonia can be reacted in the presence of hydrogen at from 100° to 500° C., preferably from 150° to 300° C., particularly preferably from 180° to 250° C., and from 10 to 500, preferably from 30 to 400, particularly preferably from 35 to 300, bar over a heterogeneous catalyst.

Suitable heterogeneous catalysts are those which contain, as catalytically active material, from 20 to 85, preferably from 25 to 80, particularly preferably from 30 to 75, % by weight of $ZrO_2$ and/or $Al_2O_3$, from 1 to 30, preferably from 2 to 25, particularly preferably from 4 to 20, % by weight of oxygen-containing compounds of copper, such as copper(I) oxide and copper (II) oxide, preferably copper (I) oxide, particularly preferably copper(II) oxide, calculated as CuO, from 1 to 40, preferably from 1 to 30, particularly preferably from 1 to 20, % by weight of oxygen-containing compounds of cobalt, such as cobalt(I) oxide and cobalt(II) oxide, preferably cobalt(I) oxide, particularly preferably cobalt(II) oxide, calculated as CoO, and/or oxygen-containing compounds of nickel, such as nickel(I) oxide and nickel(II) oxide, preferably nickel(I) oxide, particularly preferably nickel(II) oxide, calculated as NiO, and/or oxygen-containing compounds of molybdenum, preferably molybdenum(V) oxide, particularly preferably molybdenum(VI) oxide, calculated as $MoO_3$.

Ammonia is used, as a rule, in gaseous or liquid form, but in general not in aqueous solution, in a molar ratio of ammonia to triethanolamine II of from 1:1 to 50:1, preferably from 1.5:1 to 30:1, particularly preferably from 2:1 to 20:1. The ammonia excess may readily even be greater than 50:1.

The hydrogen is fed to the reaction in general in an amount of from 5 to 400, preferably from 50 to 200, l(S.T.P.) per mol of triethanolamine.

In practice, the reaction is carried out by feeding the triethanolamine and ammonia simultaneously, at the desired reaction temperature and the desired pressure, to the heterogeneous catalyst, which is usually present in a fixed-bed reactor which is preferably externally heated. The space velocity of the heterogeneous catalyst is in general from 0.01 to 5.0, preferably from 0.1 to 2.0, particularly preferably from 0.2 to 1.5, l of triethanolamine per liter of heterogeneous catalyst per hour.

It is advantageous to heat the reactants, preferably to the reaction temperature, before they are fed into the reaction vessel.

The reactor may be operated by the liquid phase or the trickle-bed procedure, ie. the reactants can be passed both upward and downward through the reactor.

The reaction can be carried out both batchwise and continuously. In both cases, the excess ammonia can be circulated together with the hydrogen. If the conversion of the reaction is not complete, the unconverted starting material can also be recycled to the reaction zone.

After the reacted mixture has been let down to atmospheric pressure, the excess ammonia and the hydrogen can be removed from said mixture, and the cyclization product obtained can be purified by distillation. Ammonia and hydrogen can advantageously be recycled to the reaction zone. The same applies to any unconverted triethanolamine.

The water of reaction formed in the course of the reaction does not in general have an adverse effect on the conversion, the reaction rate, the selectivity and the catalyst life and can therefore be left in the reaction product until the latter is worked up by distillation, at which stage said water is advantageously removed. The N-(2-hydroxyethyl)-piperazine I is used, for example, as an intermediate for the synthesis of active ingredients and crop protection agents and in particular for the preparation of 1,4-diazabicyclo

[2.2.2]octane (DABCO), a catalyst for the preparation of polyurethanes (U.S. Pat. No. 3,166,558).

EXAMPLE

Triethanolamine is fed, together with $NH_3$ and $H_2$, via a preheater to the high-pressure reactor which is operated by the liquid-phase method and has an internal temperature of from 220° to 230° C. A gentle exit gas stream (50 l per h per l of catalyst) is advantageously operated for removing inert materials.

The reactor is filled with a catalyst having the composition $ZrO_2$ (10% of CoO, 10% of NiO and 4% of CuO on a $ZrO_2$ carrier, reduced with hydrogen, finally at 400° C.). The molar ratio of triethanolamine to ammonia is 1:1.3, and the space velocity of the catalyst is 1.485 kg of triethanolamine and 0.22 kg of ammonia per l of catalyst per hour.

The mixture discharged from the oven is let down in 2 stages in a medium-pressure separator and worked up by distillation. Excess $NH_3$ and unconverted triethanolamine (25%) are recycled after being separated off by distillation.

| GC analysis of the discharged amination mixture (ammonia- and water-free [% by area] | |
|---|---|
| Monoethanolamine | 0.1% |
| Diethanolamine | 0.5% |
| Piperazine | 12% |
| N-(2-Hydroxyethyl)piperazine (HEP) | 60% (HEP:AEP = 80:20) |
| N-(2-Aminoethyl)piperazine (AEP) | |
| Aminoethylethanolamine | 1.4% |
| Triethanolamine (TEA) | 25% |
| Others | about 1% |

The reaction has been carried out by a continuous method to date. The catalyst lives are satisfactory. Thus, at the setting described (triethanolamine/ammonia=1:1.3/220° C., 200 bar $H_2$), for example, a life of 4 months was observed without any dramatic loss of activity (minus 10–20%) and without any loss of selectivity based on HEP.

The HEP/AEP ratio may vary. Decreasing the triethanolamine/ammonia ratio, for example to 1:10, is sufficient to give an HEP/AEP ratio of 20:80.

We claim:

1. A process for the preparation of N-(2-hydroxyethyl)-piperazine which comprises: reacting triethanolamine with ammonia in gaseous or liquid form, using a molar ratio of ammonia to triethanolamine of from 1:1 to 50:1, in the presence of hydrogen at from 100° to 500° C. and from 10 to 500 bar over a heterogeneous catalyst in which the catalytically active material contains from 20 to 85% by weight of $ZrO_2$ or $Al_2O_3$ or mixtures thereof, from 1 to 30% by weight of at least one copper oxide, calculated as CuO, and from 1 to 60% by weight of at least one oxide of cobalt, nickel or molybdenum, calculated as CoO, NiO and $MoO_3$, respectively.

2. A process as claimed in claim 1, wherein the reaction is carried out at from 150° to 300° C.

3. A process as claimed in claim 1, wherein the reaction is carried out at from 180° to 250° C.

4. A process as claimed in claim 1, wherein the reaction is carried out at from 30 to 400 bar.

5. A process as claimed in claim 1, wherein the reaction is carried out at from 35 to 300 bar.

6. A process as claimed in claim 1, wherein copper(II) oxide is used as the copper oxide.

7. A process as claimed in claim 6, wherein cobalt(II) oxide is used as the cobalt oxide.

8. A process as claimed in claim 6, wherein molybdenum(VI) oxide is used as the molybdenum oxide.

9. A process as claimed in claim 1, wherein the catalytically active material of the heterogeneous catalyst consists of from 25 to 85% by weight $ZrO_2$ or as a carrier for 2 to 25% by weight of said copper oxide and 1 to 20% by weight of said at least one oxide of cobalt, nickel or molybdenum.

10. A process as claimed in claim 1, wherein the catalyst consists of $ZrO_2$ as the carrier for a mixture of cobalt and nickel oxides.

11. A process as claimed in claim 1, wherein hydrogen is introduced to the reaction in an amount of from 5 to 400 liters (S.T.P.) per mol of triethanolamine.

12. A process as claimed in claim 1, wherein hydrogen is introduced to the reaction in an amount of from 50 to 200 liters (S.T.P.) per mol of triethanolamine.

13. A process as claimed in claim 1, wherein the molar ratio of ammonia to triethanol amine is 1.5:1 to 30:1.

14. A process as claimed in claim 1, wherein the molar ratio of ammonia to triethanol amine is 2:1 to 20:1.

* * * * *